(12) United States Patent
Ben-Haim et al.

(10) Patent No.: US 6,233,484 B1
(45) Date of Patent: May 15, 2001

(54) APPARATUS AND METHOD FOR CONTROLLING THE CONTRACTILITY OF MUSCLES

(75) Inventors: Shlomo Ben-Haim; Nissim Darvish; Yuval Mika, all of Haifa; Maier Fenster, Petachtikva, all of (IL)

(73) Assignee: Impulse Dynamics N.V., Curacao (AN)

(*) Notice: Subject to any disclaimer, the term of this patent is extended or adjusted under 35 U.S.C. 154(b) by 0 days.

(21) Appl. No.: 09/254,994
(22) PCT Filed: Jul. 9, 1997
(86) PCT No.: PCT/IL97/00231
  § 371 Date: Mar. 12, 1999
  § 102(e) Date: Mar. 12, 1999
(87) PCT Pub. No.: WO98/10828
  PCT Pub. Date: Mar. 19, 1998

Related U.S. Application Data
(60) Provisional application No. 60/026,392, filed on Sep. 16, 1996.

(30) Foreign Application Priority Data
Sep. 17, 1996 (IL) .......................................... 119261

(51) Int. Cl.[7] .................................................. A61N 1/365
(52) U.S. Cl. .................................................................. 607/9
(58) Field of Search .................................... 607/9, 11, 68

(56) References Cited

U.S. PATENT DOCUMENTS

| | | |
|---|---|---|
| 4,554,922 | 11/1985 | Prystowsky et al. . |
| 5,083,564 | 1/1992 | Schlerlag . |
| 5,800,464 | 9/1998 | Kieval . |
| 5,814,079 | 9/1998 | Kieval . |
| 5,871,506 | 2/1999 | Mower . |

FOREIGN PATENT DOCUMENTS

| | | |
|---|---|---|
| 0727241 | 8/1996 | (EP) . |
| WO 97/25098 | 7/1997 | (WO) . |
| WO 98/10831 | 3/1998 | (WO) . |
| WO 98/10832 | 3/1998 | (WO) . |

OTHER PUBLICATIONS

H. Antoni, et al., Polarization Effects of Sinusoidal 50–Cycle Alternating Current on Membrane Potential of Mammalian Cardiac Fibres, Pflugers Arch. 314, pp. 274–291 (1970).

H. Antoni et al., Polarization Effects of Sinusoidal 50–Cycle Alternating Current on Membrane Potential of Mammalian Cardiac Fibres, Pflugers Arch. 314, pp. 274–291 (1970).

Josephson, "Clinical Cardiac Electrophysiology: Techniques and Interpretations", 2nd Ed., R.K. Russy Ed., Ch. 16 "Surgical and Non–surgical Ablation in the Therapy of Arrhythmias".

Primary Examiner—Jeffrey R. Jastrzab
(74) Attorney, Agent, or Firm—Cowen, Liebowitz & Latman, P.C.; William H. Dippert

(57) ABSTRACT

An apparatus comprises circuitry for creating a non-excitor electric potential between at least two points located in the vicinity of a muscle. A method is provided which employs the apparatus for reducing the contraction force of a muscle.

52 Claims, 11 Drawing Sheets

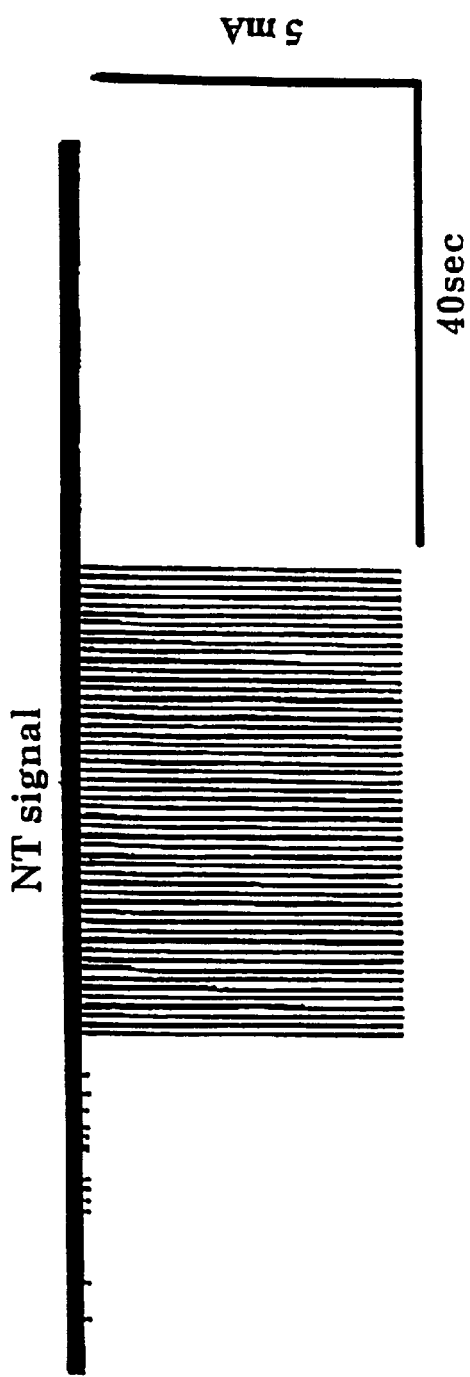
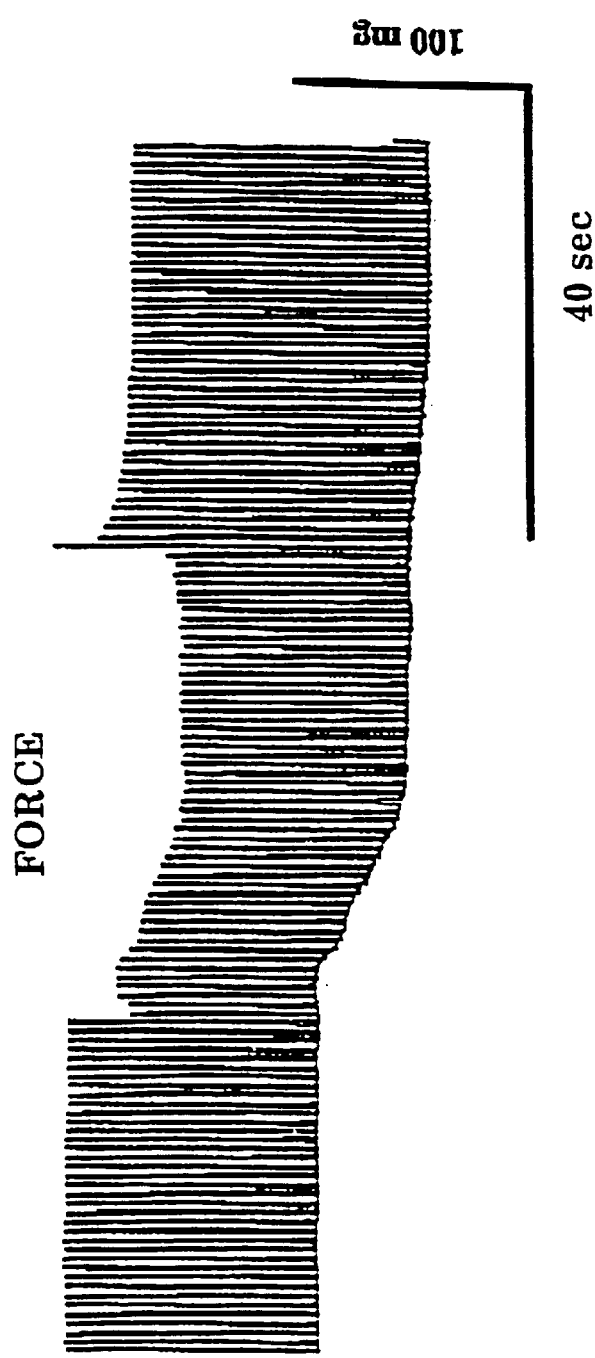

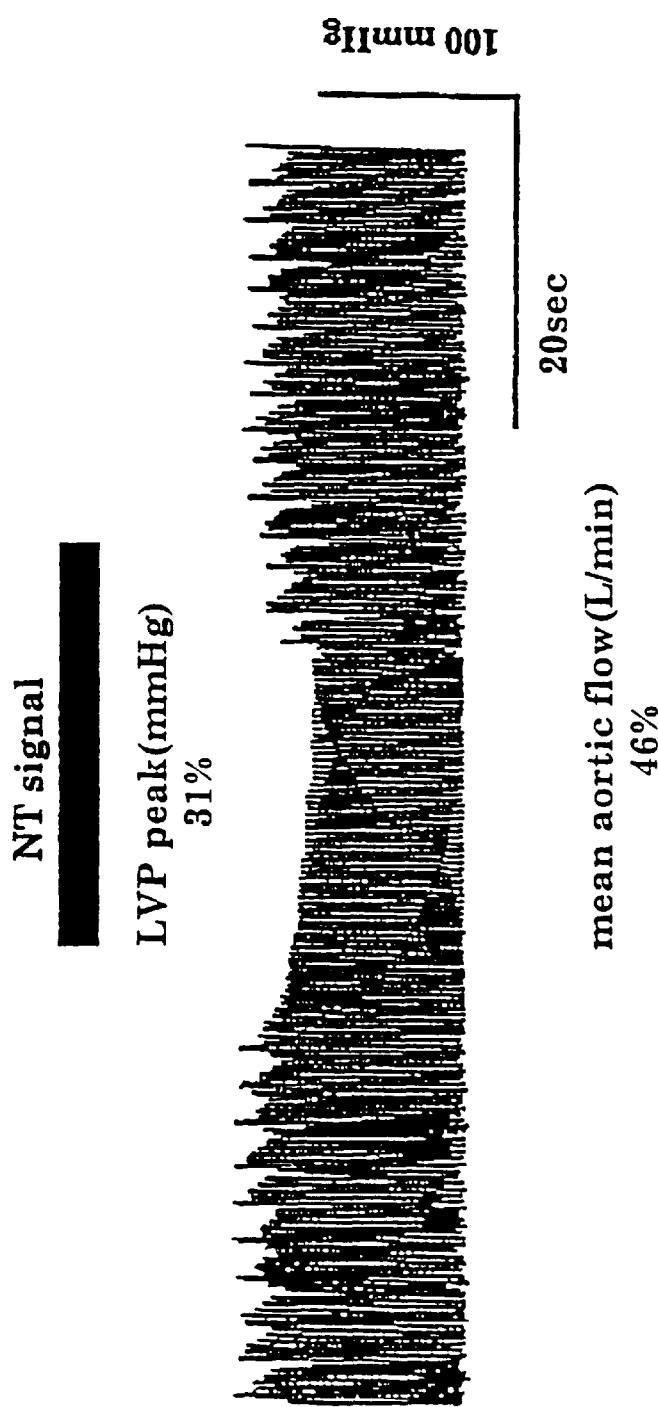
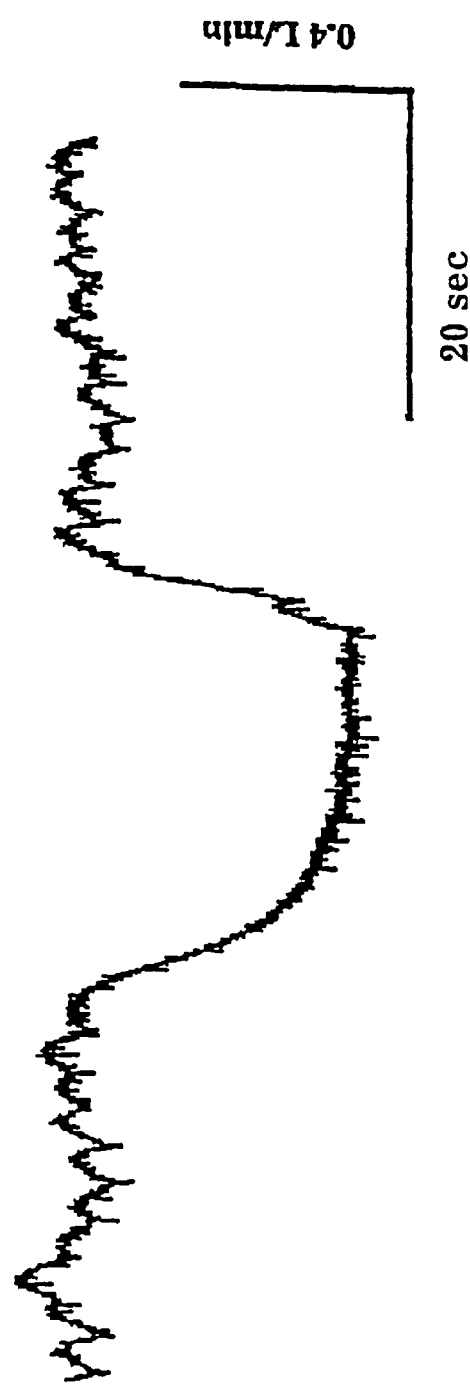

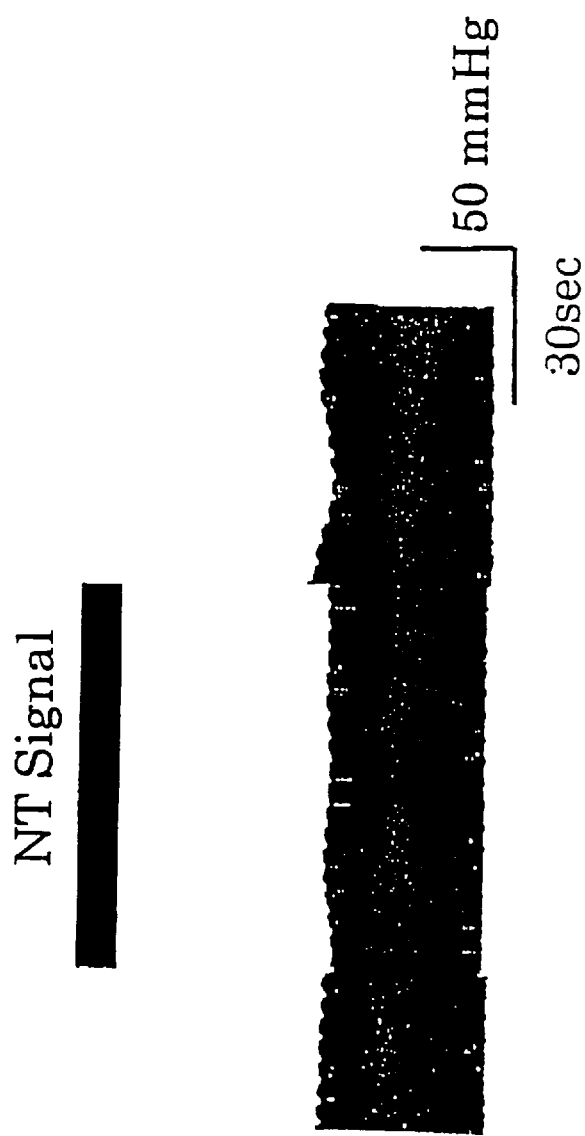

NT Signal
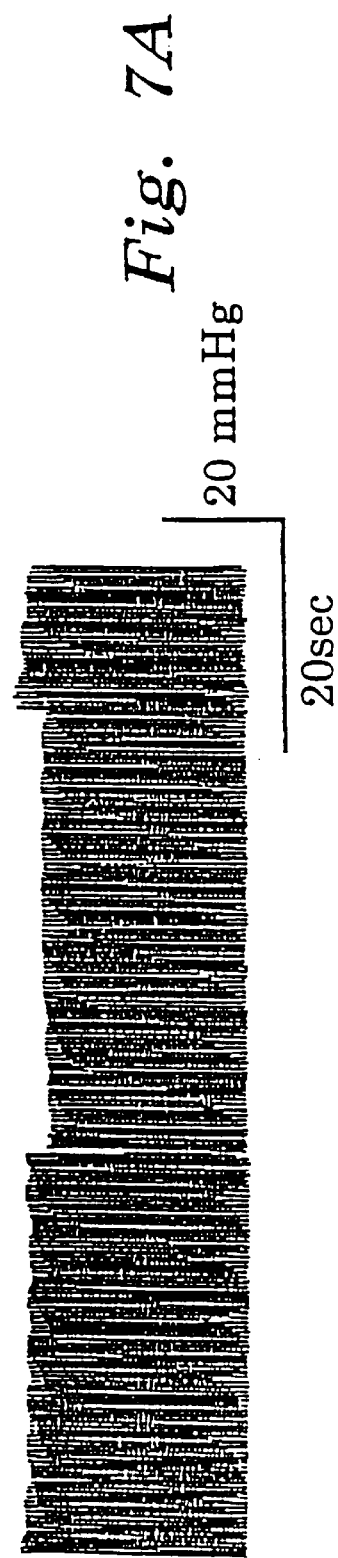
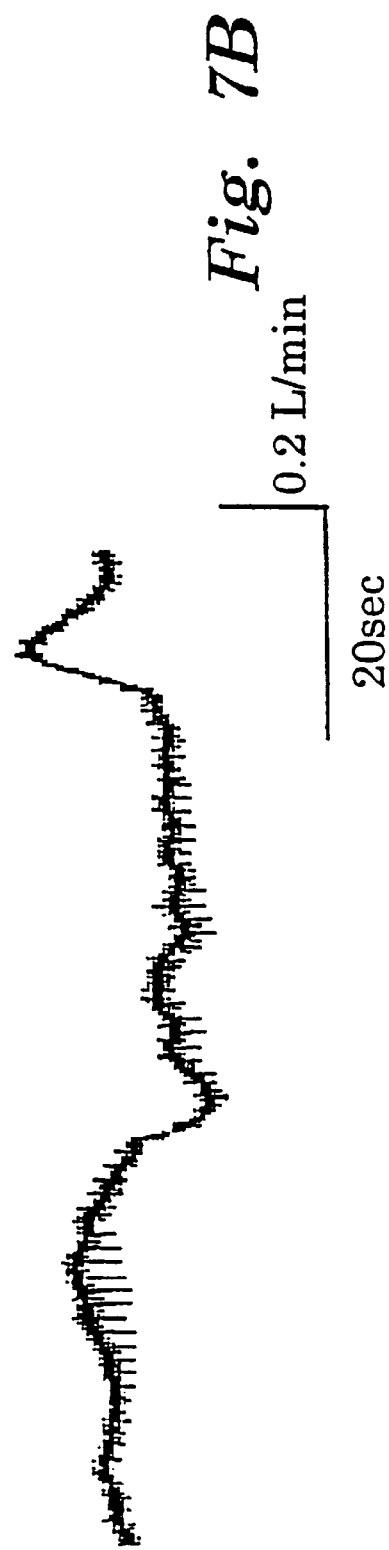

APPARATUS AND METHOD FOR CONTROLLING THE CONTRACTILITY OF MUSCLES

This application claims the benefit of Provisional Application No. 60/026,392, filed Sep. 16, 1996.

FIELD OF THE INVENTION

The present invention relates to the field of medicine. More particularly, the invention relates to means for controlling the contractility of muscles.

BACKGROUND OF THE INVENTION

Many activities of the human body involve the contraction of muscles. For instance, movement of the limbs, breathing activity, etc. The most complex and vital muscular activity of the human body is that of the heart, which functions as a pump and which, by contracting at the required times and in the required manner, controls the flow of blood throughout the body.

The heart is composed of different parts, which contract differently and with different timing, in order to permit the aforementioned pumping activity. The contraction of the heart is controlled by electric stimuli, which are generated at the cellular level by chemical reaction. However, it is well known in the art to control such activity, i.e., the timing of the contraction of the cardiac muscle, by the action of externally applied electric stimuli, through the so-called "pace maker".

In a copending PCT patent application of the same applicants herein, No. PCT/IL97/00012, filed Jan. 8, 1997, the specification of which is incorporated herein by reference, there is described a method and apparatus for increasing the contraction force of at least a portion of a heart chamber, which method comprises applying a non-excitatory electric field, for a predetermined period of time, at a delay after activation, which causes the contraction force to be increased. Substantial increases in the force of contraction are obtained, typically—but non-limitatively—in the order of 5%–50%. The increase in cardiac output is useful in order to obviate cardiac insufficiency due to a variety of pathological situations, e.g., the reduction of cardiac output due to the implantation of a pace maker, the insufficiency due to the results of the malfunctioning of a portion of the cardiac muscle, etc.

While means are now available in order to control, improve and increase the activity of the heart, not enough attention has been paid in the art to the reduction of heart muscle contractility, and no means have been provided for controlling the heart in a localized and reversible manner. The ability to control the reduction of heart muscle contractility, however, is of paramount importance in a great many situations, some of which are listed below:

Heart Surgery:

Heart surgery, as performed according to the known art, requires that ventricular fibrillation be induced on the patient's heart, and that the patient be connected to a heart and lung machine, in order to perform various operations, e.g., a bypass operation. The need to induce of ventricular fibrillation not only complicates the surgery and renders it expensive, but also increases the danger of post-operation trauma, such as the formation of thrombi and emboli. It is therefore clear that it would be highly desirable to be able to perform heart surgery, such as bypass operations, without the need to induce ventricular fibrillations, and without side effects of cardioplagia, by controllably and reversibly reducing the activity of the cardiac muscle, in the area where the operation is performed, to a level which makes it possible for the surgeon to operate with the required degree of accuracy. This is also important in performing minimal invasive surgery using thoracoscope, to enable the surgeon to better control the operation.

Healing of the Cardiac Muscle:

Reduction of the cardiac muscle contractility is of importance during the healing of the cardiac muscle after myocardial infarct. According to the known art there are no means which permit a selective reduction of the contractility of an affected area, so as to reduce the oxygen consumption of a hibernated area, so as to help them to overcome the critical period and heal. The hibernating myocardium is temporary "asleep" and can wake up to restore the function when the blood supply is restored. However, a healing period can be necessary, in which oxygen demand must be kept low.

Treating Congenital and Acquired Hypertrophic Cadiomyopathy (HCM):

The ability to reduce muscle contractility can be of importance in the treatment of this disease, which is characterized by a dynamic pressure gradient in the subaortic area that divides the left ventricle into a high-pressure apical region and a lower-pressure subaortic region. The ability to reduce muscle contractility is therefore useful to obviate this disproportion and to reduce the pressure gradient.

Cardiac Ablation:

Cardiac ablation is a procedure by which the cardiac muscle is treated by burning off selected and localized areas with a laser light or other energy source. A detailed discussion of cardiac ablation techniques can be found, e.g., in the reference book by Mark E. Josephson: "*CLINICAL CARDIAC ELECTROPHYSIOLOGY, Techniques and Interpretations*", 2nd Edition, R. Kenneth Russy Ed., Ch. 16: "*Surgical and Nonsurgical Ablation in the Therapy of Arrhythmias*" Lea & Febiger, Malvern, Pa. The ablation is performed on a beating heart, and the art has so far failed to provide means by which the contractility, i.e., the movement, of the treated area can be reduced.

Selective Contractility Reduction:

While it is known in the art to reduce the contractility of the heart as a whole, by means of systemic drugs, the art so far has not been able to provide means by which a desired portion of the heart can be caused to reduce its contractility, which other portions function with an unchanged contractility, or even with a contractility which has been increased as described and claimed in the aforementioned PCT patent application. This option, unavailable according to the known art, is important in order to compensate for the temporary reduction in contractility of one area, by the increased contractility of another.

Interim Treatment:

In many cases, e.g., intractable angina, there is a need to reduce oxygen consumption of the cardiac muscle while treatment is being considered. The known art does not provide any means to reduce the contractility of the heart muscle in a localized manner, thus reducing the oxygen consumption until other treatment is initiated.

It is therefore highly desirable to provide means which permit the reduction of the contractility of the cardiac muscle, in an controlled manner. It is an object of the present invention to provide apparatus and a method by which the contractility of a portion of the cardiac muscle can be reduced in a controlled manner.

It is another object of the invention to provide apparatus and a method for facilitating cardiac surgery on a beating heart.

It is still another object of the invention to provide apparatus and a method for promoting the healing of the hibernated area of the cardiac muscle after myocardial infarct.

It is yet another object of the invention to provide apparatus and a method for selectively reducing the oxygen consumption of a portion of a heart.

Other objects and advantages of the invention will become apparent as the description proceeds.

SUMMARY OF THE INVENTION

The invention relates to apparatus comprising circuitry for creating a non-excitatory electric potential between at least two points located in the vicinity of a muscle.

In the context of the present invention, the terms "non-excitatory current", or "non-excitatory potential", or "non-excitatory signals", mean a signal which does not cause a propagating action potential in the muscle cells (which may start a new pacing or contraction of the muscle). In other words, the non-excitatory electric stimulation effected by a non-excitatory electric pulse is such that it does not induce propagating activation potentials in the cardiac muscle cells. Rather, such pulses affect the response of the heart muscle to the action potentials, by modulating cell contractility within selected segments of the cardiac muscle. As described in the abovementioned PCT patent application PCT/IL97/00012, the inventors have found that by applying non-excitatory electrical stimulation pulses of suitable strength, appropriately timed with respect to the heart's electrical activation, the contraction of the selected segments can be increased or decreased, thus increasing or decreasing the stroke volume of the heart.

There may be various reasons for a signal to be non-excitatory. Two main types of non-excitatory signals to be used in conjunction with the invention are: 1) A signal which, independently of its magnitude, is applied during the refractory period, and therefore does not cause a new contraction, even though its magnitude may be above threshold values for pacing; 2) A signal which is sub-threshold for pacing and, therefore, no matter when applied, does not cause a new contraction to take place.

According to one embodiment of the invention, the apparatus comprises circuitry for controlling the start time of the electric potential generated between said at least two points. According to another preferred embodiment of the invention the apparatus comprises circuitry for controlling the duration of the electric potential generated between said at least two points. According to yet another preferred embodiment of the invention the apparatus comprises circuitry for controlling the magnitude of the electric potential generated between said at least two points.

In another aspect, the invention is directed to apparatus comprising circuitry for causing a non-excitatory electric current to flow between at least two points located in the vicinity of a muscle.

According to one embodiment of the invention, the apparatus comprises circuitry for controlling the start time of the electric current flowing between said at least two points. According to another preferred embodiment of the invention the apparatus comprises circuitry for controlling the duration of the electric current flowing between said at least two points. According to yet another preferred embodiment of the invention the apparatus comprises circuitry for controlling the magnitude of the electric current flowing between said at least two points.

The apparatus according to the invention, as described above, is suitable for use in reducing the contraction force of a muscle, such as a cardiac muscle.

The circuitry for creating a non-excitatory electric potential between said at least two points may be of many different types and preferably comprises one or more electrode. Illustrative and non-limitative examples of suitable electrodes include carbon electrodes.

The apparatus of the invention may be provided in various forms and may be, e.g., an insertable device, an extra corporal device or an implantable device.

According to a preferred embodiment of the invention the circuitry for controlling the start time and/or duration of the electric potential is synchronized to heart activity. Furthermore, such circuitry may operate not at every beat of the heart, e.g., every 1, 2 or 3 beats of the heart.

According to a preferred embodiment of the invention the non-excitatory electric current is a DC electric current. According to a preferred embodiment of the invention, the apparatus further comprises signal generation circuitry for superimposing on the DC signal one or more waveforms of given frequency and amplitude, thereby to generate a complex signal.

The apparatus according to the invention is particularly useful for performing heart surgery, such as a bypass operation.

The apparatus of the invention is also useful in many other applications, such as for promoting the healing of the hibernated area of the cardiac muscle after myocardial infarct, for promoting the healing of an ischemic area of the cardiac muscle, for treating congenital or acquired hypertrophic cardiomyopathy, and for aiding in performing cardiac ablation.

In another aspect the invention is directed to apparatus for reducing the contraction force of a muscle, comprising:

means for creating an electric potential between at least two points located in the vicinity of the muscle;

means for causing a non-excitatory DC electric current to flow between said at least two point, if desired; and means for controlling the start time, duration and magnitude of the non-excitatory electric potential and/or of the non-excitatory electric current flowing between said at least two points.

According to a preferred embodiment of the invention the apparatus comprises:

means for creating an electric potential between at least a pair of electrodes in the vicinity of the muscle at at least two root locations;

means for causing a non-excitatory DC electric current to flow between said at least two root locations when desired; and means for controlling the start time, duration and magnitude of the non-excitatory electric potential and/or of the non-excitatory electric current flowing between said at least two root locations.

By "root location" it is meant to indicate the vicinity of the muscle where the electrodes are located, which may be distinct from the area which is affected by the current flowing between them. As will be appreciated by the skilled person, due to the very complex nature of the electric behavior of the cardiac muscle, it is possible that positioning an electrode at a given location will affect another, more remote portion of the muscle. Therefore, the root location is not necessarily the center or any other portion of the treated area, but it is only a location, near the muscle, where an electrode will be positioned.

In yet another aspect, the invention is directed to a method for reducing the contraction force of a muscle, comprising creating a non-excitatory electric potential between at least two points located in the vicinity of the muscle, and controlling one or more of the parameters consisting of start time, duration, magnitude and polarity of the non-excitatory electric potential created between said at least two points.

In still a further aspect, the invention is directed to method for reducing the contraction force of a muscle, comprising causing a non-excitatory electric current to flow between at least two points located in the vicinity of the muscle, and controlling one or more of the parameters consisting of start time, duration, magnitude and polarity of the non-excitatory electric current flowing between said at least two points.

The non-excitatory electric signal can be a DC signal and further a complex signal can be generated by superimposing on the DC signal one or more waveforms of given frequency and amplitude. According to a preferred embodiment of the invention the non-excitatory DC electric signal is synchronized to heart activity, and can be imparted not at every beat of the heart, e.g., every 1, 2 or 3 beats of the heart.

Also encompassed by the invention is a method for performing heart surgery, comprising reducing the contraction force of a treated area of the cardiac muscle, according to the invention, and thereafter performing surgery thereon.

The invention can be usefully exploited in a variety of situations involving heart surgery, such as in a bypass operation.

Additionally, according to the invention there is provided a method for promoting the healing of the cardiac muscle after myocardial infarct, comprising creating a non-excitatory electric potential between at least two points located in the vicinity of the muscle, and controlling one or more of the parameters consisting of start time, duration, magnitude and polarity of the non-excitatory electric potential created between said at least two points, said electric potential being of an intensity and polarity suitable to obtain the desired reduction in muscle contraction at the affected heart area.

In another preferred embodiment of the invention there is provided a method for promoting the healing of the cardiac muscle after myocardial infarct, comprising causing a non-excitatory electric current to flow between at least two points located in the vicinity of the muscle, and controlling one or more of the parameters consisting of start time, duration, magnitude and polarity of the non-excitatory electric current flowing between said at least two points, said electric current being of an intensity and polarity suitable to obtain the desired reduction in muscle contraction at the affected heart area.

The invention further provides a method for treating congenital or acquired hypertrophic cardiomyopathy, comprising reducing the contraction force of a the heart muscle, according to the invention, for a suitable period of time.

The invention is also useful in performing other procedures, such as for performing cardiac ablation, by reducing the contraction force of the area of the cardiac muscle to be ablated, and thereafter performing the ablation thereon.

It should also be noted that, when the reduction in contractility is effected on a localized area, it is possible, and it may be useful in some cases, to increase the cardiac muscle contractility at locations other than the treated location. This can be effected as described in greater detail in the aforementioned PCT application PCT/IL97/00012.

In another aspect, the invention is directed to a method for the interim treatment of a heart in need of reducing oxygen consumption, comprising reducing the contraction force of a the heart muscle, according to the invention, thereby reducing the oxygen consumption of the heart.

According to a preferred embodiment of the invention, there is provided a method for reducing the contraction force of a muscle, comprising:

providing means for creating an electric potential between at least two points located in the vicinity of the muscle;

providing means for causing a non-excitatory DC electric current to flow between said at least two point;

providing means for switching the current polarity between said at least two points; and providing means for controlling the start time, duration and magnitude of the electric current flowing between said at least two points.

According to one preferred embodiment of the invention, there is further provided a method, comprising:

providing an electric potential between at least a pair of electrodes in the vicinity of the muscle at at least two root locations;

causing a non-excitatory DC electric current to flow between said at least two contacting locations;

providing means for switching the current polarity between said root locations; and controlling the start time, duration and magnitude of the electric current flowing between said at least two root locations, so as to obtain the desired reduction in muscle contraction.

The apparatus employed to carry out the method of the invention can be of different construction, as will be apparent to the skilled person. One example of apparatus suitable for carrying out the invention is described in detail and claimed in a copending PCT patent application of the same applicants herein, entitled "Cardiac Output Controller", filed on the same day as the present application and identified as Attorney's Docket 27068, the description of which is incorporated herein by reference. Another example of suitable apparatus, coupled to a pacemaker device, is the subject of another copending PCT patent application of the same applicants herein, entitled "Cardiac Output Enhanced Pacemaker", filed on the same day as the present application and identified as Attorney's Docket 27181, the specification of which is also incorporated herein by reference. However, as said, the invention is not intended to be limited to any particular construction of device used to carry it out.

As said, while a DC current is typically used as the base line for the non-excitatory signal, it is possible, and in some applications it may be desirable, to supply a signal which is a complex signal, for instance, a signal generated by superimposing an AC current on the DC base signal, so as to generate a waveform of varying envelope. Any suitable signal can be superimposed, having any shape, e.g., square wave or sinusoidal wave, as will be apparent to the skilled person. Thus, according to one preferred embodiment of the invention the apparatus further comprises means for superimposing on the DC signal one or more waveforms of given frequency and amplitude, thereby to generate a complex signal.

It should also be appreciated that the apparatus of the invention operates with synchronization of the cardiac activity, since lack of synchronization may result in ventricular fibrilation. Synchronization of the NT-signal can be effected on the pacing signal, if a pace maker or other pacing apparatus is used, or to the cardiac activity of the patient. In the examples to follow a pacing signal is used, for the sake of precision in operation of the muscle the activity of which is being sampled.

As will be appreciated by the skilled person, the actual set of operating parameters used (current, length of pulse, number of electrodes, lag after pacing signal, etc.), will be dependent on the specific use made of the invention, and the skilled person will be able to devise the optimal set of parameters for a given application. Some non-limitative operating ranges in which cardiac muscle reacts according to the invention are given here for the sake of illustration only, it being understood that operation outside such ranges is of course possible under various conditions: Current: 0.01–10 mA; Length of Pulse: 1–998 milliseconds with a pacing of 1 Hz, and 1–498 milliseconds with a pacing of 2 Hz; Delay after Pacing Signal: 1 milliseconds and above. Where no pace maker is used, the delay is preferably calculated from the natural pacing of the patient's heart, or from the local activation time of the muscle.

As stated, while the invention can be exploited with other muscles, the most important muscle to be treated according to the invention is the cardiac muscle. While a variety of electrodes can be used, and the invention is in no way limited to any particular type of electrode, particularly preferred suitable electrodes for this purpose are, e.g., carbon electrodes.

As will become apparent to the skilled person by the description to follow, the determination of the optimal parameters for a given subject can be easily be effected at the beginning of any given procedure and progressively adjusting the various parameters (current intensity, pulse duration, time lag from pacing), so as to reach the desired decrease in cardiac contractility. Of course, other parameters may be optimized by the physician on a given patient, in order to obtain the best performance when reducing the contractility of the muscle. Such parameters include, e.g., the distance between the root location of the electrodes, and the surface area of the electrodes. The distance will influence the size of the area that is affected by the electric current, and when the root locations are placed far apart, a stronger current may be required. Of course, larger electrodes (with greater surface area) may be needed to deliver more current. As will be apparent to the skilled person, the area affected by the signal may be very small (e.g., 2 $cm^2$, or substantially the whole heart can be affected, as illustrated in FIG. 7, described in detail below.

BRIEF DESCRIPTION OF THE DRAWINGS

The above and other characteristics and advantages of the invention will be more readily apparent through the following detailed description of preferred embodiments thereof, with reference to the appended drawings, wherein:

FIG. 2 shows the results obtained in Example 1:

FIG. 2A shows the timing and magnitude of the electric signal (NT-signal); and

FIG. 2B shows the force of contraction of the muscle;

FIG. 4 shows the results obtained in Example 2:

FIG. 5 shows the results obtained in Example 3:

FIG. 5A shows the decrease in LVP pressure;

FIG. 5B shows the decrease in output (mean aortic flow);

FIG. 6 shows the results obtained in Example 4:

FIG. 6A is the decrease in LVP pressure;

FIG. 6B is the decrease in output (blood flow rate);

FIG. 7 shows the results obtained in Example 5:

FIG. 7A shows the decrease in pressure;

FIG. 7B shows the decrease in blood flow rate;

DEFINITIONS

Figure 1:
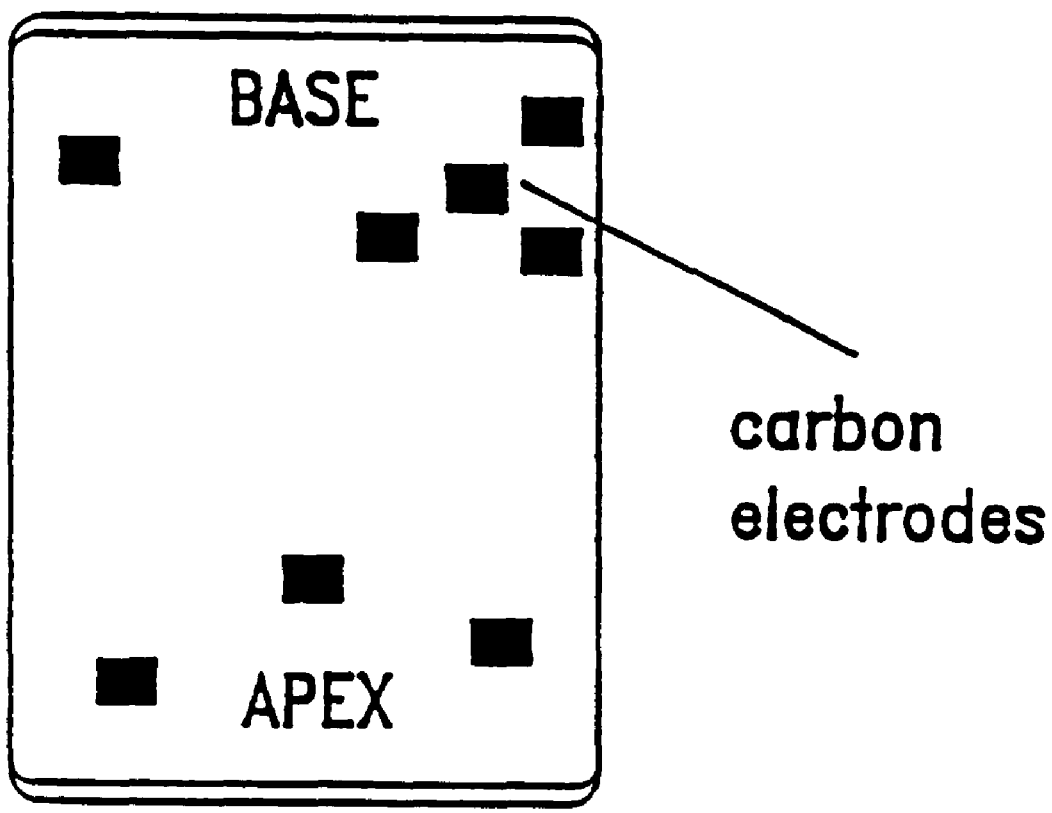
FIG. 1 is a schematic representation of the experimental setup used in the Acute Cardiac Inhibition experiments in anaesthetized dogs (such as used in the experiments detailed in FIG. 5)

The following terms and abbreviations, used throughout this specification, are defined below, for the sake of clarity:

b.p.m.=Beats per minute

HMC=Hypertrophic Cardiomyopathy

I.M.=Intramuscular

IV=Intra Venous

LV=Left Ventricle

LVP=left ventricular pressure

NT Signal=Non-Excitatory Signal

RV=Right Ventricle

VF=Ventricular Fibrillation

DETAILED DESCRIPTION OF PREFERRED EMBODIMENTS

The invention will now be illustrated through in vitro and in vivo experiments. Experiments in vitro were carried out using isolated rabbit papillary muscle, and the protocol for its isolation is detailed below. Experiments in vivo were carried out on dogs, and the protocol for such experiments is also detailed below.

Isolated Papillary Muscle Protocol

Animals:

New Zealand white rabbits (males) from Israel (Yokneam) or an hybrid of New Zealand White and local albino rabbits (males, AniLab, Rehovot) are kept in room temperature, 2–3 per cage (35×55×65 cm), under natural light conditions. Daily feeding of dry food (Rabbit Mix—Code 590), and unlimited water supply. The cages and the room are cleaned daily, Instruments:

A. For Solution Making:

Scales (by Mettler toledo, model P8303, Max 310 gram, d=1 mGram) magnetic stirrer, by Freed electric. Weights 10 Kg (d=50 gram) by Moznei Shekel, Gas tanks with mixed 95% $O_2$+5% $CO_2$" pressure regulators, pH meter by Mettler Toledo, model 320 PH, ice machine 45 Labotal.

B. For the In-Vitro Papillary Muscle Preparation

Dissection chamber (HSH, Hugo Sachs Elektronik, Germany), Steered organ bath type 813 (I-18E) including temperature controller type 319, Force Transducer type F30 with amplifier type 660 and calibration unit (HSE), Stereoscope (Olympus, Japan), Digital micro manipulator (HSE), Manipulator, Anti-vibration table (TMC, USA), Faraday cage, Fiber optic illuminator (HSE), Current and Voltage clamp amplifier (axon Instruments, USA), stimulators (grass instruments, USA), Micro-pipette puller model pp-83 (Narishige, Japan) Current source ISO 10 and ISO-50 (home made) supplying 10 and 50 mA correspondingly and Oscilloscope, 20 MHz (Gould, England), Computers: PowerPC 9500/I50, (Apple, USA), or Pentium, 166 MHz, Data Acquisition Boards: PCI-MIO-16XE50, 16 bite, or the PCI-MIO-16E-2, 12 bite board by National Instrument, software: LabView for windows, by National Instrument (USA). Data acquisition and analysis program are home made, The program includes data acquisition and on-line analysis, programmable experiment execution, programmable signal output. The off-line analysis program analyze different parameters of muscle twitch and action potentials.

Solution:

The Krebs-Heseleit Solution (KHS) was prepared using materials from Sigma (Israel): 0.32 g/lit KCl (4.5 mM), 6.99 g/lit NaCl (118.0 mM), 2.01 g/lit $NaHCO_3$ (24.0 mM), 0.285 g/lit $MgSO_4.7H_2O$ (1.19 mM), 0.16 g/lit $KH_2PO_4$ (1.18 mM), 2.0 g/lit Glucose (11.0 mM), and 0.37 g/lit $CaCl_2.2H_2O$ (2.52 mM), added after bubbling with a 95% $O_2$+5% $CO_2$ gas mixture for 20 minutes.

Solution preparation: Distilled water (ion exchange column Zilion, Israel and ultra filtration by EasypurLF, Israel) are used to prepare the KHS stock solution (X 20, 5 L). The chemicals except $CaCl_2$ are used. The stock solution is discarded after 1 week of refrigeration, For each day of experiment fresh solution is prepared (5 L) out of the stock solution, $CaCl_2$ is added, and the solution is bubbled (95% $O_2$/5% $CO_2$) for 20 min. and titrated to a pH of 7.4. Bubbled KHS at room temperature is used for perfusion of the papillary muscle kept in an organ bath.

Anesthesia and Heart Dissection:

animal is brought from the cage to a scale for measuring body weight, The animal is anesthetized by 1Vembutal 1–1.2 mg/Kg body weight I.P, using-5 cc syringe and 23 Gage needle. The level of anesthesia is checked by the animal reflex to a pinch. When the animal is deeply anesthetized, the skin over the chest is cut off and the chest wall is cut open exposing the heart. Using scissors and a forceps the pericardium is cut and the heart is dissected out by cutting all the blood vessels, Immediately after cutting, the heart is placed in an ice cold (4° C.) and oxygenated KHS.

Papillary Muscle Dissection:

The heart is transferred to a fresh ice-cold KHS and than to the dissection chamber, containing ice-cold continuously oxygenated KHS. The heart is fixed to a rubber pad with insect pins and than the left ventricle is opened exposing the papillary muscles. A silk (6 0) thread is tied around the tendon of the papillary muscle and the muscle is dissected out using fine twizers. The dissected muscle (length of 2–3 mm) is transferred to the organ bath and the heart is kept at 4° C. for further dissections of the other papillary muscles.

The Steiert Organ Bath:

The muscle is placed in an organ bath, and than fixed to the chamber by a plastic holder. The silk thread tied to the tendon is hooked to a rigid hook on the force transducer (on the opposite side) to give isometric conditions. The papillary muscle is continuously perfused (7–12 ml/min,) with oxygenated KHS kept at a regulated temperature of 37° C.

Pacing and Stimulation:

Pacing stimuli (typically 1 Hz, 2 ms duration, and amplitude of 2 mA) are given by two Ag—AgCl electrodes which are part of the organ bath and are placed under the muscle. The electrodes are covered with AgCl layer, chlorodizing by 5 mA, 5 ms pulses during perfusion. Constant current stimuli (NT-signal) are given to the upper part of the muscle using graphite electrodes (diameter of 0.5 mm fitted to a glass pipette) placed 2–3 mm apart along the fibers' line (contraction axis). The muscle length is adjusted to maximal isometric force and left for equilibration period of 30 min.

Protocol for Acute Experiments

Cardiac Inhibition

Equipment:

The following equipment which will be referred to hereinafter, is now briefly described for the sake of clarity:

Plugsys System:

The plugsys system is an incorporating plug in modules for measuring, controlling and data processing in connection with recorders and computers. In general, it functions as an amplifier which increases the sensitivity of the measuring of biological signals. One such device, used in the experiments described herein, is manufactured by HSE, Germany.

Millar:

This device (manufactured by Millar Instruments, USA), is a micro manometers transducer that can be connected to a battery operated bridge (which is the interface box) and the output can be digitized using an A/D converter. In another mode of operation the transducer is connected through a DBA (plugsys DC Bridge Amplifier), which is an amplifier connected to transducers to measure pressure force (manufactured by HSE, Germany).

1. Premedication and Anesthesia 1.1 Dogs are premedicated (sedated) with morphine sulfate (2 mg/kg) I.M.

1.1.1. Wait 30 min.

1.2 Open 2 IV lines 1.2.1 Anesthesia is performed using α-chloralose: (freshly prepared in the morning of the experiment using: 2 gr. sodium tetraborate, 6 gr. α-chloralose and 30 gr. of urethane dissolved in 300 cc water heated to 60° C. and than cooled to 37° C. before IV administration). A good anesthetic level is achieved when the corneal reflex is absent.

1.3. Infuse 500 cc Ringer Lactate during the first 15 min. after accomplishment of anesthesia. Continuous infusion of Ringer Lactate at a rate of 5 cc/min via the second IV line.

1.4. Continuous anesthesia is given with a pump charged with a 50 cc syringe filled with α-chloralose-urethane solution at an infusion rate of 0.15 cc/min.

2. Mechanical Ventilation

Immediately after the animal is anesthetized artificial ventilation is set on, The animal is intubated using an endotracheal tube (#7–8.5) and ventilated with room air at 14–20 rpm, output phase ratio 50%, stroke volume between 300–400 cc (depending on dog size).

3. Hemodynamic Measurements 3.1. EKG: Remove hair from areas where EKG patches are positioned, at both anterior legs and left posterior leg.

3.2. Open Arterial Line: The right and left femoral artery are exposed and introducer sheets (8.5F) are inserted. The introducer sheet are prewashed with saline-heparin (2500 units/dl).

3.3 Millar Transducer Calibration: 7F Millar pressure transducers are used for measuring both left ventricular pressure (LVP) and arterial blood pressure (BP).

3.4 Blood Pressure: BP is obtained from another Millar transducer introduced into the other femoral artery after calibration, 3.5 Jugular Veins: the left jugular vein is exposed and 8.5–9F introducer sheet is applied to insert a pacing electrode into the right ventricle under X-Ray if needed.

3.6 Left Ventricular Catheterization: Using X-ray the Millar catheter is inserted into the LV.

4. Surgical Procedures 4.1 Monitoring Heart Rate. Heart rate is carefully monitored before chest opening. Rise in the heart rate upon chest opening is prevented by administration of Fentanyl Citrate (3–4 µg/kg IV) 5–10 min. before incision is made.

4.2 Chest Incision. Chest is opened through a middline incision with a diathermic-cauterizing blade set to the lowest possible power. The blade is used to cut the skin and muscle layers above the sternum. Bleeding is promptly stopped to achieve stabilization of animal hemodynamics. The chest is maintained open with a retractor for only short periods as needed. Body temperature is controlled with an infrared lamp 50–80 cm above the chest area.

5. Electrical and Hemodynamic Monitoring 5.1 Aortic Flow. Aortic flow (cardiac output) is measured by placing a Transonic Doppler flow meter transducer on the thoracic descending aorta. Calibrate the ultrasound probe in a plastic cup filled with saline to zero flow while 'Mea' button is pressed. Check that the appropriate key for each probe is connected to the Transonic flow meter (model T106, TRANSONIC, USA). Once the reading is zero it can be placed and secured with a screw driver (probes of 6, 10 and 12 mm). The transducer yields averaged and pulsate blood flows into the acquisition system.

5.2. Arterial Blood Pressure. The Millar transducer is connected to a Plugsys. The signal is filtered at 300 Hz and fed into the acquisition system.

5.3. Left Ventricular Pressure. The animal LVP is measured using a catheter tip micro manometers (Millar Instruments, USA) inserted into to the left ventricle either throughout the left or right femoral artery. The micro manometers transducer is connected to a battery operated bridge and the output will be digitized using A/D converter.

5.4 EKG. Surface EKG is measured using the standard EKG leads connected to the animal limbs. The signal is amplified with a BPA unit (bipotential amplifier module for direct measurement of EKG, manufactured by HSE, Germany) on a Plugsys amplifier.

6. Data Acquisition

Sampling is carried using National Instruments AT-MIO data acquisition board. The board allows simultaneous acquisition up to 8 differential channels. The sampling rate is up to 200 KHz. The sampling used in the system is 1 KHz per channel. The acquired data can be displayed on line on the computer monitor and saved on the computer disk for further data analysis. The printouts shown in the figures were obtained from the above setup.

7. Detailed Description of the Experimental Setup:

A bipolar pacing electrode was inserted into the heart and placed near the apex of the RV using an X-Ray. Carbon screw electrodes (home made) were placed at the base (epicardially) of the LV and three at the apex as schematically illustrated in FIG. 1.

Acquisition Setup:

Channel 0=NT signal

Channel 1=LVP

Channel 2=Mean Aortic flow

Channel 3=EKG-body surface

Channel 4=Blood pressure

Channel 5=Pulsate aortic flow

Channel 6=Changed according to the protocol

Channel 7=Pacing

EXAMPLE 1

In Vitro Effect of Polarity of Muscle Contraction

Papillary muscle tissue was removed from the left ventricle of a rabbit, according to the protocol described above. The tissue was placed in a Steiert Organ Bath Type 813 (HSE, Germany) in which the experiment was carried out.

The muscle was excited at a rate of 1 pulse per second (1 Hz). The polarity of the NT signal was inverse to that which caused an increase in the muscle contractility.

The muscle was caused to contract by the application of a pacing signal at 1 Hz, 4 millisecond duration of 2 mA amplitude. 5 Milliseconds after the pacing signal, a non-excitatory signal of 5 milliampers was applied during 150 milliseconds. The result is shown in FIG. 2, which shows the timing and magnitude of the electric signal (NT-signal—FIG. 2A), and the force of contraction of the muscle, measured as explained above (FIG. 2B).

Figure 3A:
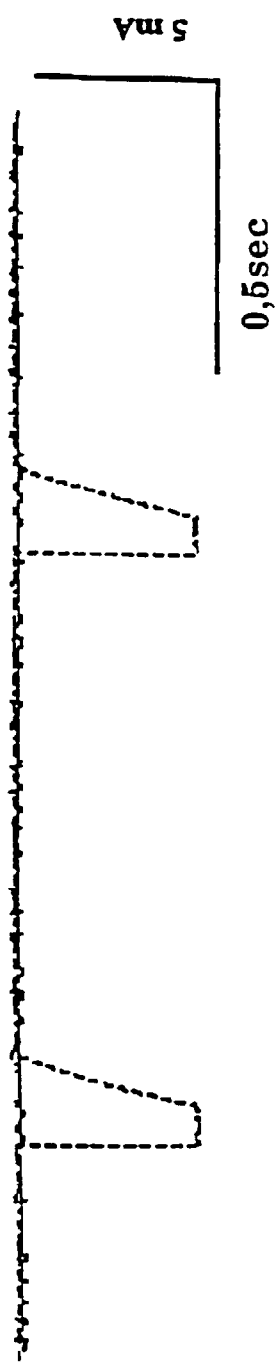
FIGS. 3 (A, B) shows the results obtained in the same experimental setup of Example 1, but on a different time scale.
Figure 3B:
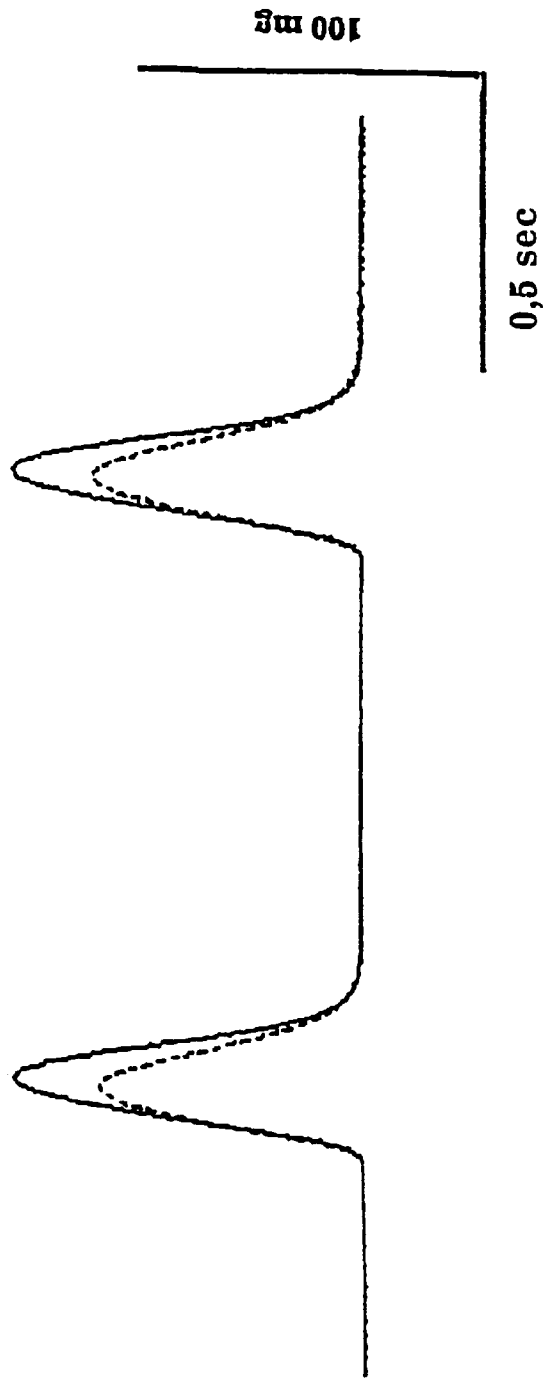

The same experiments as in FIG. 2 are shown in FIG. 3, with higher time resolution, showing only the effect of NT-signal application on two muscle contractions (twitches). The dashed line represents the contraction force when the NT signal is applied.

EXAMPLE 2

Figure 4A:
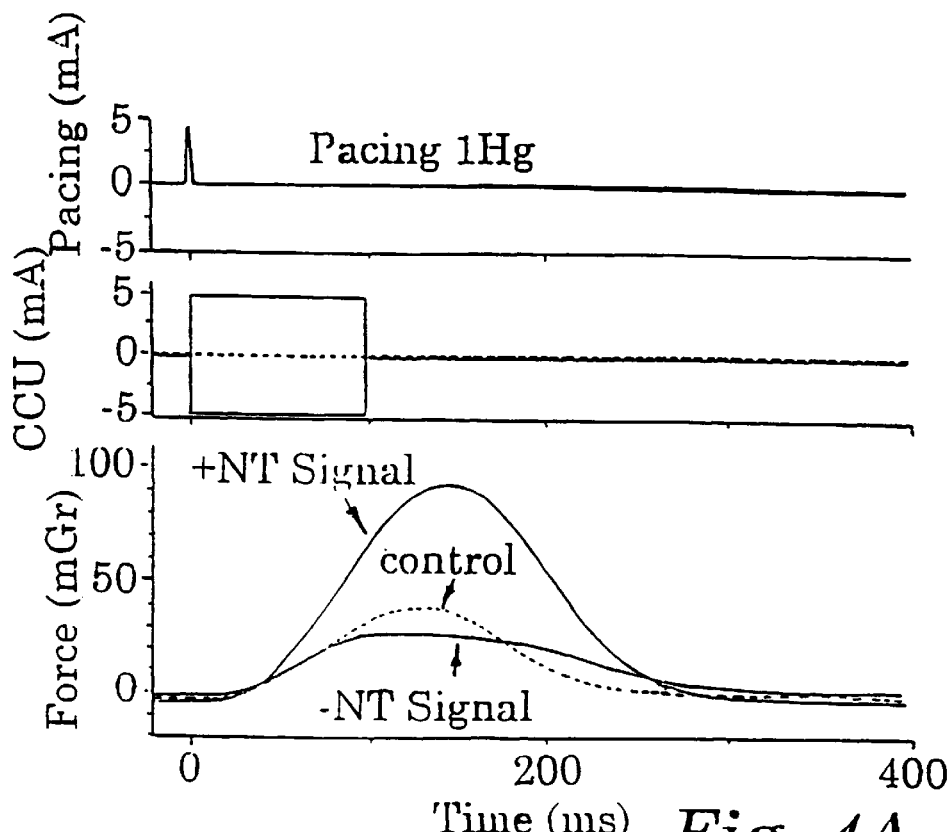
FIG. 4A shows the behavior of the force in the different situations.
Figure 4B:
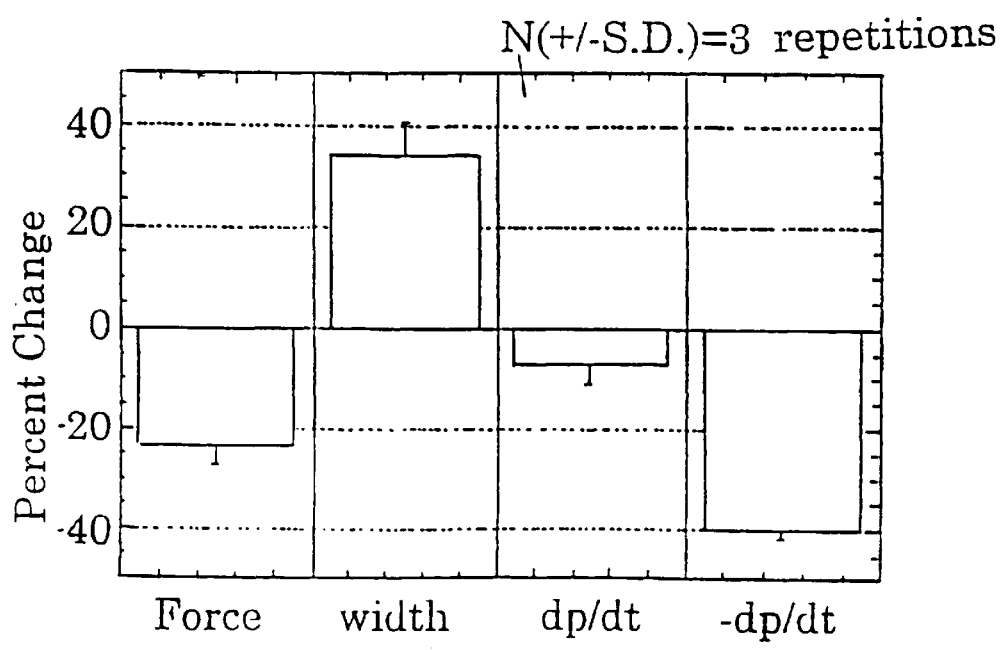
FIG. 4B shows a summary of data from three experiments where decrease in muscle contractility was achieved by changing the polarity of the signal.

Example 1 was repeated while on the same muscle tissue, with a pacing of 1 Hz, a pacing signal of 4 mA for a period of 2 milliseconds. The non-excitatory signal (NT-signal) of 5 mA was applied with a 5 mS delay, and for 100 miliseconds thereafter. Three different situations were tested: "+NT-signal", with a positive polarity "−NT-signal", with a negative polarity, and "Control", without the application of a NT-signal. The signs of the polarity are taken so that "+NT-signal" indicates an increase in contractility, and "−NT-signal" indicates a decrease in contractility. The results are shown in FIG. 4, where FIG. 4A shows the behavior of the force in the different situations, and FIG. 4B shows a summary of data from three experiments where decrease in muscle contractility was achieved by changing the polarity of the signal, going from left to right: there is a decrease of over 20% in peak force compared to the control, there is a 35% increase in the contraction width as measured at 10% of base-peak, there is a decrease in dp/dt (in the papillary muscle dp/dt means the rate of change in the development of contraction force), which represents the developing of force in the ascending limb of the twitch (an increase in dp/dt is considered an increase in contractility), but there is a very significant decrease in −dp/dt, which is the relaxation from the twitch (descending limb of the twitch) indicating reduction in the efficacy of the muscle contraction.

EXAMPLE 3

A dog was prepared for an in-vivo experiment, as described in detail in the above Protocol. The dog's heart was paced using a pace maker, at 160 heartbeats per minute. Carbon electrodes were positioned at the base of the left ventricle (cathode) and at the edge of the ventricle (anode), and a current was caused to flow between them 60 milliseconds after the pacing signal was delivered to the right ventricle. The current was 8 mA, and was continued for 50 milliseconds. The current pulse caused a reduction in heart output, as well as in the contractility of the cardiac muscle cells, as calculated from the developed pressure of the left ventricle.

The results are seen in FIG. 5, where FIG. 5A shows the decrease in LVP pressure, and FIG. 5B shows the decrease in cardiac output (mean aortic flow). From both results the reduction of the contractility of the beating heart in vivo is clearly demonstrated.

EXAMPLE 4

Operating as in Example 3, The heart was simultaneously paced (150 b.p.m.) with a physiologic electrode within the apex of the right ventricle, and Medtronics epicardial electrodes at the right auricle.

LVP was measured with a Millar transducer catheter located within the left ventricle. Cardiac output was evaluated with a 12 mm ultrasonic probe (Transonic) positioned after the aortic arch in the thoracic aorta.

NT signals were delivered epicardially with electrodes located at the posterior side of the left ventricle. The apical electrode (+) was located at mid-way between the apex and the base (−). The basal electrode was positioned between Circumflex and the Right Coronary artery. The electrical current delivered was 8 mA, delay from the pacing pulse was 40 msec, and duration of the pulse was 30 msec.

Results: The results are shown in FIG. 6, in which FIG. 6A is the decrease in pressure, and FIG. 6B is the decrease in output (blood flow rate). The mean aortic flow decreased 6% relative to the baseline during the application of the NT signal. The Left ventricular pressure showed decreases in:

peak amplitude ratio: −7.6% peak width ratio: −0.3%

+dP/dt −15%

−dP/dt −25%

EXAMPLE 5

Operating as in Example 3, the heart was simultaneously paced (140 b.p.m.) with a physiologic electrode within the apex of the right ventricle, and Medtronics epicardial electrodes at the right auricle.

LVP was measured with a Millar transducer catheter located within the left ventricle, Cardiac output was evaluated with a 12 mm ultrasonic probe (Transonic) positioned after the aortic arch in the thoracic aorta.

NT signals were delivered epicardially with electrodes located at the posterior side of the left ventricle. The apical electrode (+) was located at mid-way between the apex and the base (−). The basal electrode was positioned between Circumflex and the Right Coronary arteries. The electrical current delivered was 8 mA, delay from the pacing pulse was 40 msec, and duration of the pulse was 30 msec.

Results: The results are shown in FIG. 7. FIG. 7A shows the decrease in pressure, and FIG. 7B shows the decrease in blood flow rate. The mean aortic flow decreased by 11.9% relative to the baseline during the application of the NT signal. The left ventricular pressure showed decreases in:

peak amplitude ratio: −8.6% (compared to baseline)

peak width ratio: −2.6% (compared to control)

+dP/dt: −3.9%

−dP/dt: −30.3%

EXAMPLE 6

Long Duration Sub-Critical Signal

Sub-critical non-excitatory signal (NT-signal) is a current that will not induce a new contraction in the cardiac muscle, because its amplitude is sub-critical, viz., its magnitude is not enough to cause pacing, and which therefore also meets the requirements for non excitatory signal as described above.

Long duration Sub-critical NT-signal (Sub-NT-signal) can reduce the peak force of contraction during pacing. An organ bath experiments on rabbit left ventricle papillary muscle was carried out.
Parameters:

Pacing: 1 Hz, 2 ms duration, 4 mA.

Sub-NT-signal: 5 mS delay, 995 mS, 0.5 mA.

Figure 8:
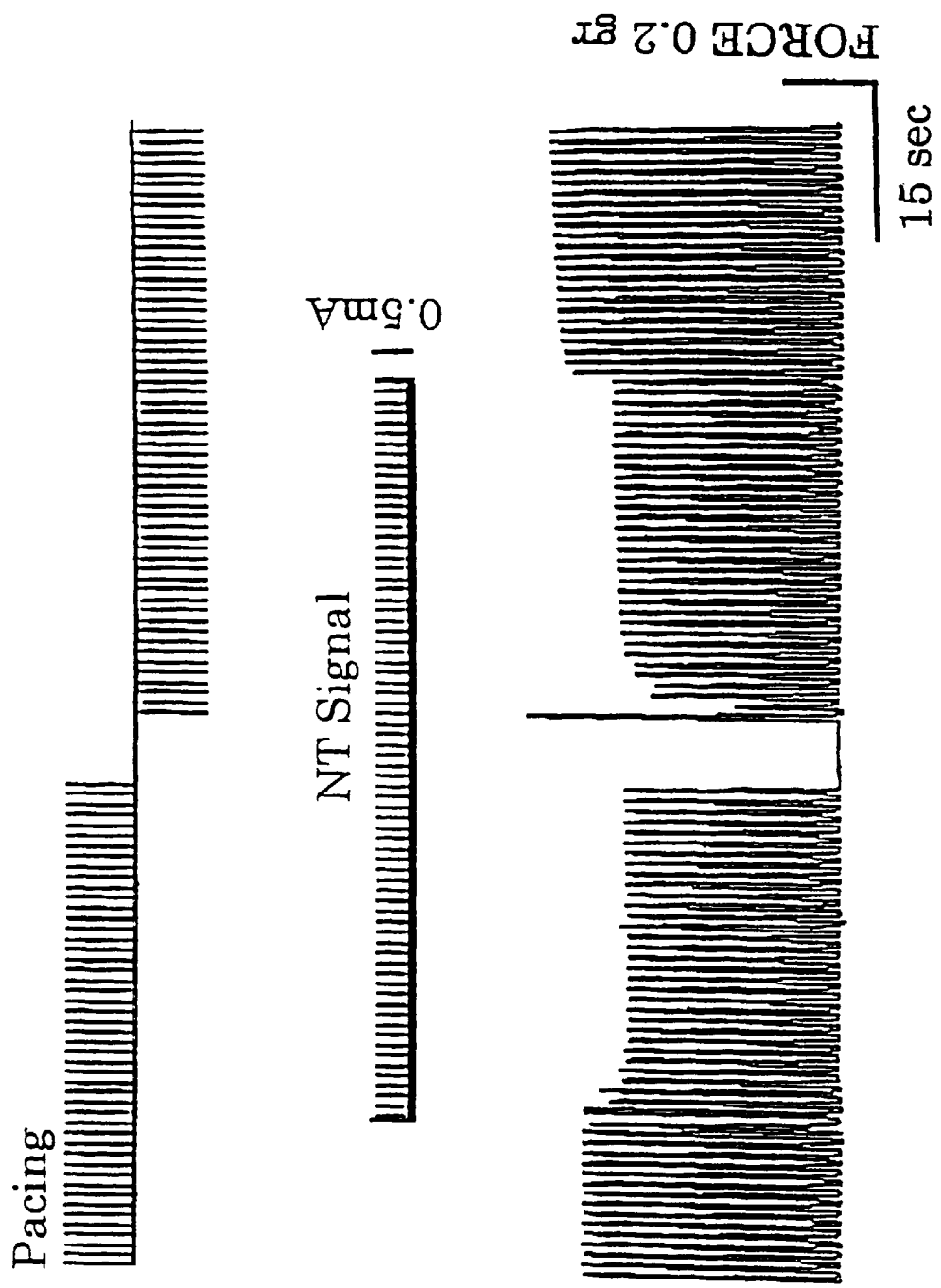
FIG. 8 shows the results obtained in Example 6.

The results are shown in FIG. 8, which shows a decrease of about 20% in the peak force induced by Sub-NT-signal during pacing. Sub-NT-signal alone does not cause contraction. This is shown in the trace when the pacing stimulation is turned off.

EXAMPLE 7

Figure 9:
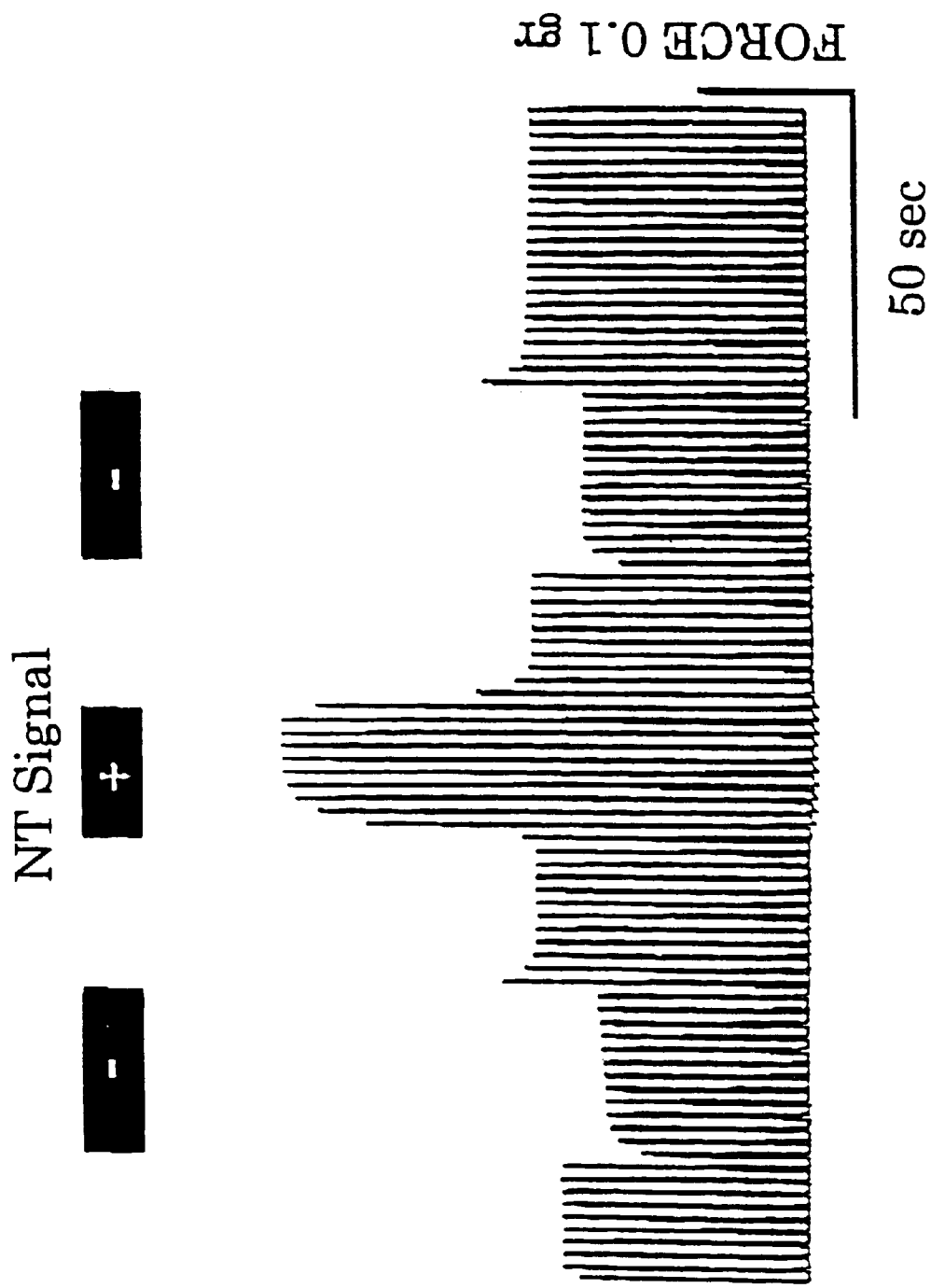
FIG. 9 shows the results obtained in Example 7.

Example 1 was repeated, under the following conditions: The muscle was paced at 1 Hz, 2 mA amplitude, 2 msec duration. NT signals were applied at 30 msec delay, 60 msec duration, and amplitude of 6 mA. The polarities were switched (+ and − signs), to show the effect of the polarity on the contractility. The results are shown in FIG. 9, from which the decrease in force of the muscle is clearly seen, when a "−" polarity is applied, and an increase when a "+" polarity is applied. Once again, the "+" and "−" signs are arbitrary, and indicate the result as detailed above.

EXAMPLE 8

Operating as in Example 1, a long duration NT-signal was applied to the left ventricular papillary muscle from rabbit. The parameters employed were:

Pacing: 0.5 Hz, 2 mS duration, 3.5 mA.

NT-signal: 1 mS delay, 1999 mS duration, 10 mA.

Figure 10:
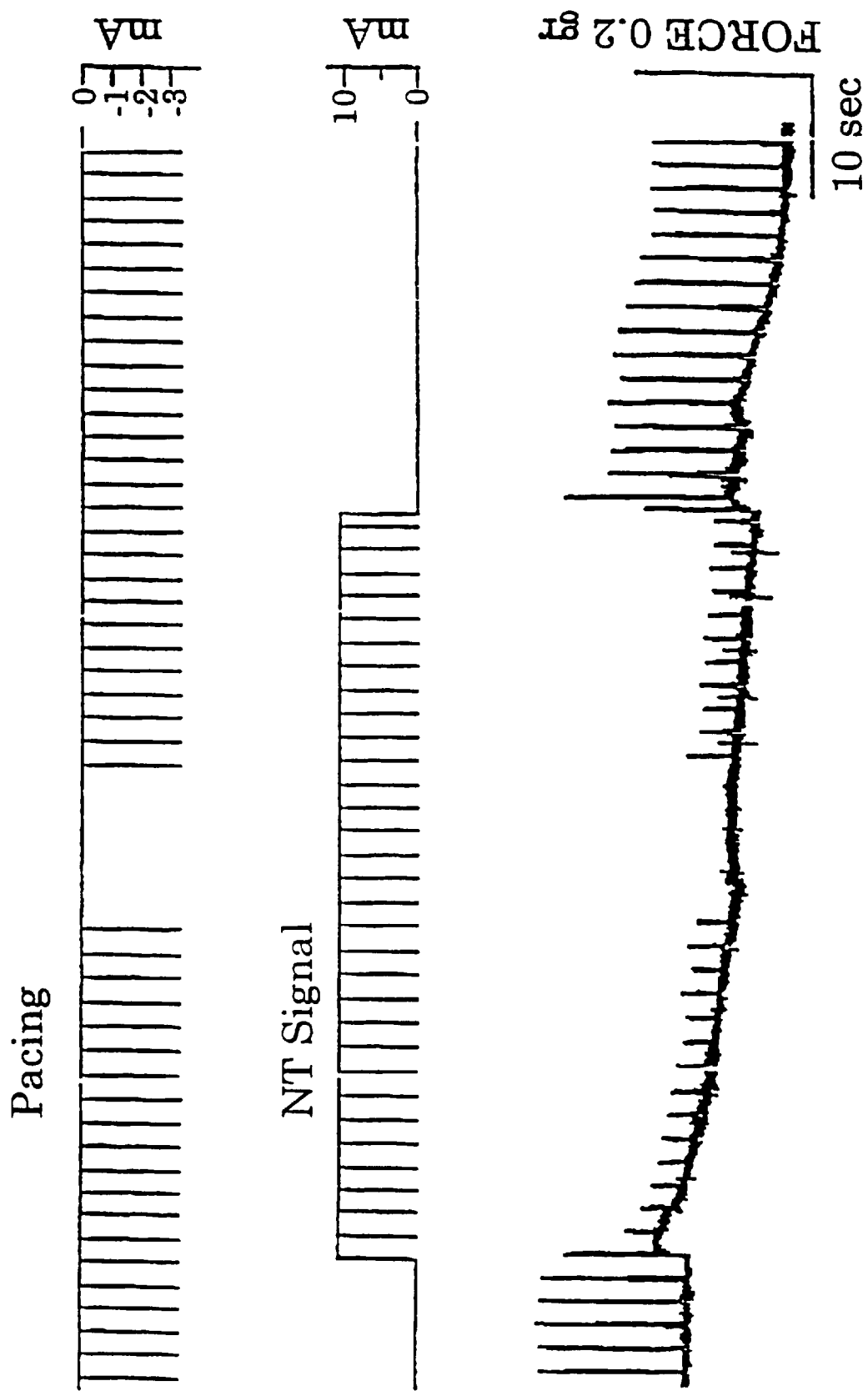
FIG. 10 shows the effect of applying a long NT-signal.

The results are shown in FIG. 10, from which it can be seen that an about 75% decrease in peak force is induced by the NT-signal during pacing. Stopping pacing (upper trace), but not the NT signal (middle trace) stopped the muscle contraction (lower trace).

It should be noted that the non-excitatory nature of the NT signal employed in this experiment derives from its length, and not from its magnitude. Accordingly, this experiment illustrates another type of NT signal useful for reducing contractility.

Figure 11:
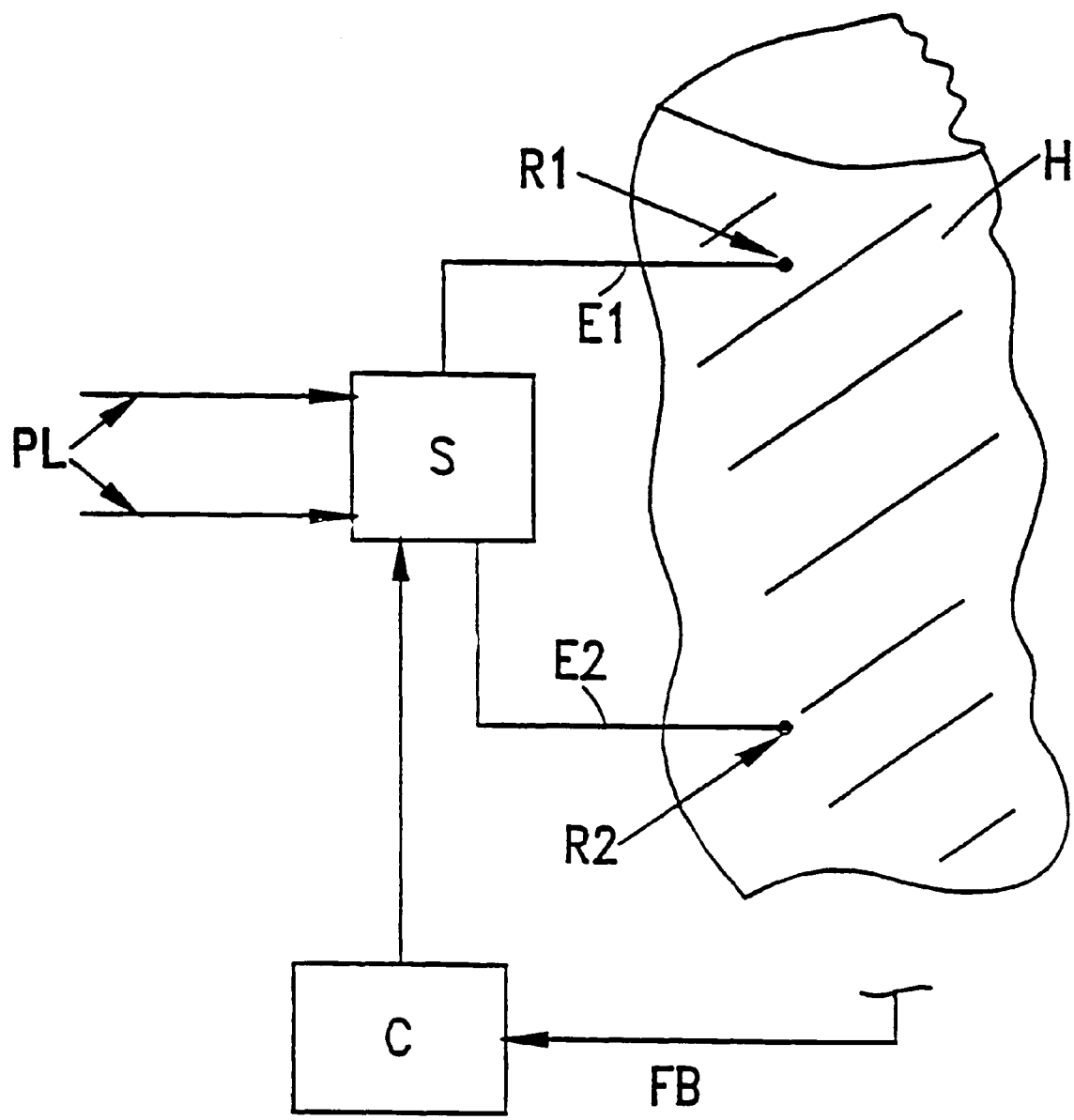
FIG. 11 is a schematic representation of an apparatus according to one embodiment of the invention.

Referring now to FIG. 11, a schematic representation of an apparatus according to one embodiment of the invention is seen. In this scheme, a portion of a cardiac muscle, H, is brought into closed positioned relationship with two electrodes, E1 and E2, the ends of which are positioned at root position R1 and R2, respectively. The electrodes receive the voltage and current from a signal generator S, the construction of which is conventional and well know to skilled persons, and which is therefore not described here in detail, which in turn receives power from a power line, PL, connected to an autonomous power source or to the mains, as the case may be. The activity of the power signal generator S is controlled by a controller, C, which may be a microprocessor, or which may be an external controlling device, e.g., a PC or other computer. The controller C controls the parameters of the signal generated by the signal generator, such as current intensity, frequency and timing, and may use both preset parameters (e.g., the frequency of pulse generation) and feed-back input, e.g., from apparatus which monitors heart or other parameters, or from a pace maker which supplies the pacing signal. These input signals are collectively schematically indicated in the figure as FB. Of course, the apparatus is only schematically shown, for the sake of brevity. And the skilled person will easily be able to devise many different kinds of apparatus suitable to supply the signal needed in carrying out the invention.

All the above description and examples have been given for the purpose of illustration, and are not intended to limit the invention in any way. Many modifications can be effected in the apparatus and method of the invention. For instance, different electrodes can be used, with different currents, for different periods of times; various areas of the heart can be provided with electrodes and treated therewith, and different devices can be provided, whether implanted or external, for temporary or continued treatment, all without exceeding the scope of the invention.

What is claimed is:

1. Apparatus comprising circuitry for creating a non-excitatory electric potential between at least two points located in the vicinity of a muscle, comprising circuitry for controlling the start time and/or the duration of the electric potential generated between said at least two points which is synchronized to heart activity, said circuitry not operating at every beat of the heart.

2. Implantable apparatus comprising circuitry for causing a non-excitatory electric current to flow between at least two points located in the vicinity of a muscle and circuitry for controlling the start time and/or duration of the electric current, wherein said circuitry for controlling does not operate at every beat of the heart.

3. Apparatus as claimed in claim 2, wherein the circuitry for controlling the start time and/or duration of the electric current operates every 2 or 3 beats of the heart.

4. Apparatus for selectively and reversibly reducing the oxygen consumption of an area of a muscle, comprising circuitry for creating a non-excitatory electric potential between at least two points located in the vicinity of the muscle, and comprising circuitry for controlling the start time and/or duration of the electric current flowing between said at least two points which is synchronized to heart activity, said circuitry not operating at every beat of the heart.

5. Apparatus for reducing the contraction force of a muscle, comprising:

means for creating an electric potential between at least two points located in the vicinity of the muscle;

means for causing a non-excitatory DC electric current to flow between said at least two point, if desired; and means for controlling the start time, duration and magnitude of the non-excitatory electric potential and/or of the non-excitatory electric current flowing between said at least two points.

6. Apparatus according to claim 5, comprising:

means for creating an electric potential between at least a pair of electrodes in the vicinity of the muscle at at least two root locations;

means for causing a non-excitatory DC electric current to flow between said at least two root locations when desired; and means for controlling the start time, duration and magnitude of the non-excitatory electric potential and/or of the non-excitatory electric current flowing between said at least two root locations.

7. A method for reducing the contraction force of a muscle, comprising creating a non-excitatory electric potential between at least two points located in the vicinity of the muscle, and controlling one or more of the parameters consisting of start time, duration, magnitude and polarity of the non-excitatory electric potential created between said at least two points.

8. A method for reducing the contraction force of a muscle, comprising causing a non-excitatory electric current to flow between at least two points located in the vicinity of the muscle, and controlling one or more of the parameters consisting of start time, duration, magnitude and polarity of the non-excitatory electric current flowing between said at least two points.

9. A method according to claim 7 or 8, wherein the muscle is a cardiac muscle.

10. A method according to claim 8, wherein the non-excitatory electric current is a DC current.

11. A method according to claim 10, further comprising generating a complex signal by superimposing on the DC signal one or more waveforms of given frequency and amplitude.

12. A method according to claim 8, wherein the flow of the non-excitatory DC electric current is synchronized to heart activity.

13. A method according to claim 12, wherein the non-excitatory DC electric current flows not at every beat of the heart.

14. A method according to claim 13, wherein the non-excitatory DC electric current flows every 2 or 3 beats of the heart.

15. A method for performing heart surgery, comprising reducing the contraction force of a treated area of the cardiac muscle, by creating a non-excitatory electric potential between at least two points located in the vicinity of the muscle, and controlling one or more of the parameters consisting of start time, duration, magnitude and polarity of the non-excitatory electric potential created between said at least two points, thereby to obtain the desired reduction in muscle contraction at the treated heart area and thereafter performing surgery thereon.

16. A method for performing heart surgery, comprising reducing the contraction force of a treated area of the cardiac muscle, by causing a non-excitatory electric current to flow between at least two points located in the vicinity of the muscle, and controlling one or more of the parameters consisting of start time, duration, magnitude and polarity of the non-excitatory electric current flowing between said at least two points, thereby to obtain the desired reduction in muscle contraction at the treated heart area and thereafter performing surgery thereon.

17. A method according to claim 15 or 16, wherein the heart surgery is a bypass operation.

18. A method according to claim 15 or 16, wherein the heart surgery is a minimally invasive cardiac operation.

19. A method for promoting the healing of the cardiac muscle after myocardial infarct, comprising creating a non-excitatory electric potential between at least two points located in the vicinity of the muscle, and controlling one or more of the parameters consisting of start time, duration, magnitude and polarity of the non-excitatory electric potential created between said at least two points, said electric potential being of an intensity and polarity suitable to obtain the desired reduction in muscle contraction at the affected heart area.

20. A method for promoting the healing of the cardiac muscle after myocardial infarct, comprising causing a non-excitatory electric current to flow between at least two points located in the vicinity of the muscle, and controlling one or more of the parameters consisting of start time, duration, magnitude and polarity of the non-excitatory electric current flowing between said at least two points, said electric current being of an intensity and polarity suitable to obtain the desired reduction in muscle contraction at the affected heart area.

21. A method for selectively and reversibly reducing the oxygen consumption of an area of a muscle, comprising causing a non-excitatory electric current to flow between at least two points located in the vicinity of the muscle, and controlling one or more of the parameters consisting of start time, duration, magnitude and polarity of the non-excitatory electric current flowing between said at least two points, said electric current being of an intensity and polarity suitable to obtain the desired reduction in oxygen consumption at the affected heart area.

22. A method for selectively and reversibly reducing the oxygen consumption of an area of a muscle, comprising creating a non-excitatory electric potential between at least two points located in the vicinity of the muscle, and controlling one or more of the parameters consisting of start time, duration, magnitude and polarity of said non-excitatory electric potential, said electric potential being of an intensity and polarity suitable to obtain the desired reduction in oxygen consumption at the affected heart area.

23. A method for treating congenital or acquired hypertrophic cardiomyopathy, comprising reducing the contraction force of the heart muscle by creating a non-excitatory electric potential between at least two points located in the vicinity of the muscle, and controlling one or more of the parameters consisting of start time, duration, magnitude and polarity of the non-excitatory electric potential created between said at least two points, said electric potential being of an intensity and polarity suitable to obtain the desired reduction in muscle contraction.

24. A method for treating congenital or acquired hypertrophic cardiomyopathy, comprising reducing the contraction force of the heart muscle by causing a non-excitatory electric current to flow between at least two points located in the vicinity of the muscle, and controlling one or more of the parameters consisting of start time, duration, magnitude and polarity of the non-excitatory electric current flowing between said at least two points, said electric current being of an intensity and polarity suitable to obtain the desired reduction in muscle contraction.

25. A method for performing cardiac ablation, comprising reducing the contraction force of the area of the cardiac muscle to be ablated, by creating a non-excitatory electric potential between at least two points located in the vicinity of the muscle, and controlling one or more of the parameters consisting of start time, duration, magnitude and polarity of the non-excitatory electric potential created between said at least two points, thereby to obtain the desired reduction in muscle contraction at the heart area to be ablated, and thereafter performing the ablation thereon.

26. A method for performing cardiac ablation, comprising reducing the contraction force of the area of the cardiac muscle to be ablated, by causing a non-excitatory electric current to flow between at least two points located in the vicinity of the muscle, and controlling one or more of the parameters consisting of start time, duration, magnitude and polarity of the non-excitatory electric current flowing between said at least two points, thereby to obtain the desired reduction in muscle contraction at the heart area to be ablated, and thereafter performing the ablation thereon.

27. A method according to any one of claims 16, 20, 21, 24 or 26, wherein the non-excitatory electric current is a DC current.

28. A method according to claim 27, further comprising generating a complex signal by superimposing on the DC signal one or more waveforms of given frequency and amplitude.

29. A method according to any one of claims 16, 20, 21, 24 or 26, wherein the flow of the non-excitatory DC electric current is synchronized to heart activity.

30. A method according to claim 29, wherein the non-excitatory DC electric current flows not at every beat of the heart.

31. A method according to claim 30, wherein the non-excitatory DC electric current to flows every 2 or 3 beats of the heart.

32. A method according to any one of claims 16 and 19 to 24, wherein the cardiac muscle contractility is increased at locations other than the treated location.

33. A method for the interim treatment of a heart in need of reducing oxygen consumption, comprising reducing the contraction force of the heart muscle by creating a non-excitatory electric potential between at least two points located in the vicinity of the muscle, of an intensity and polarity suitable to obtain the desired reduction in muscle contraction at the treated heart area, thereby reducing the oxygen consumption of the heart.

34. A method for the interim treatment of heart in need of reducing oxygen consumption, comprising reducing the contraction force of a the heart muscle by causing a non-excitatory electric current to flow between at least two points located in the vicinity of the muscle, of an intensity and polarity suitable to obtain the desired reduction in muscle contraction at the treated heart area, thereby reducing the oxygen consumption of the heart.

35. A method according to claim 34, wherein the non-excitatory electric current is a DC current.

36. A method according to claim 35, further comprising generating a complex signal by superimposing on the DC signal one or more waveforms of given frequency and amplitude.

37. A method according to claim 34, wherein the flow of the non-excitatory DC electric current is synchronized to heart activity.

38. A method according to claim 37, wherein the non-excitatory DC electric current flows not at every beat of the heart.

39. A method according to claim 38, wherein the non-excitatory DC electric current flows every 2 or 3 beats of the heart.

40. A method for reducing the contraction force of a muscle, comprising:
providing means for creating an electric potential between at least two points located in the vicinity of the muscle;
providing means for causing a non-excitatory DC electric current to flow between said at least two point;
providing means for switching the current polarity between said at least two points; and
providing means for controlling the start time, duration and magnitude of the electric current flowing between said at least two points.

41. A method according to claim 40, comprising:
providing an electric potential between at least a pair of electrodes in the vicinity of the muscle at at least two root locations;

causing a non-excitatory DC electric current to flow between said at least two contacting locations;

providing means for switching the current polarity between said root locations; and controlling the start time, duration and magnitude of the electric current flowing between said at least two root locations, so as to obtain the desired reduction in muscle contraction.

42. A method according to claim 40 or 41, further comprising generating a complex signal by superimposing on the DC signal one or more waveforms of given frequency and amplitude.

43. A method according to claim 40 or 41, wherein the means for causing a non-excitatory DC electric current to flow, are synchronized to heart activity.

44. A method according to claim 43, wherein the means for causing a non-excitatory DC electric current to flow operate not at every beat of the heart.

45. A method according to claim 44, wherein the means for causing a non-excitatory DC electric current to flow operate every 2 or 3 beats of the heart.

46. Apparatus for performing heart surgery, comprising circuitry for creating a non-excitatory electric potential between at least two points located in the vicinity of the heart muscle and circuitry for controlling the start time and/or duration of electric current flowing between said at least two points which is synchronized to heart activity, wherein said circuitry for controlling does not operate at every beat of the heart.

47. Apparatus for promoting the healing of the hibernated area of the cardiac muscle after myocardial infarct, comprising circuitry for creating a non-excitatory electric potential between at least two points located in the vicinity of the muscle, comprising circuitry for controlling the start time and/or duration of the electric current flowing between said at least two points which is synchronized to heart activity, said circuitry not operating at every beat of the heart.

48. Apparatus for promoting the healing of an ischmeic area of the cardiac muscle, comprising circuitry for creating a non-excitatory electric potential between at least two points located in the vicinity of the muscle, comprising circuitry for controlling the start and/or duration of the electric current flowing between said at least two points which is synchronized to heart activity, said circuit not operating at every beat of the heart.

49. Apparatus for treating congenital or acquired hypertrophic cardiomyopathy, comprising circuitry for creating a non-excitatory electric potential between at least two points located in the vicinity of the muscle, comprising circuitry for controlling the start time and/or duration of the electric current flowing between said at least two points which is synchronized to heart activity, said current not operating at every beat of the heart.

50. Apparatus for aiding in performing cardiac ablation, comprising circuitry for creating a non-excitatory electric potential between at least two points located in the vicinity of the muscle, comprising circuitry for controlling the start time and/or duration of the electric current flowing between said at least two points which is synchronized to heart activity, said circuitry not operating at every beat of the heart.

51. Apparatus according to any one of claims 4 and 47–50, wherein the circuitry for controlling the start time and/or duration of the electric current operates every 2 or 3 beats of the heart.

52. Apparatus according to any one of claims 4, 46, and 47–50, wherein the non-excitatory electric current is a DC current, further comprising signal generation circuitry for superimposing on the DC signal one or more waveforms of given frequency and amplitude, thereby to generate a complex signal.

* * * * *